US010597462B1

(12) United States Patent
Valance-Washington et al.

(10) Patent No.: US 10,597,462 B1
(45) Date of Patent: Mar. 24, 2020

(54) ANTI-TLT-1 ANTIBODY AND USES THEREOF

(71) Applicants: Anthony Valance-Washington, Bayamon, PR (US); Yancy Ferrer-Acosta, Cupey, PR (US); Jessica Morales, Vega Alta, PR (US); Fiorella Reyes-Baez, Cupey, PR (US)

(72) Inventors: Anthony Valance-Washington, Bayamon, PR (US); Yancy Ferrer-Acosta, Cupey, PR (US); Jessica Morales, Vega Alta, PR (US); Fiorella Reyes-Baez, Cupey, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 16/242,995

(22) Filed: Jan. 8, 2019

Related U.S. Application Data

(60) Provisional application No. 62/582,994, filed on Nov. 8, 2017.

(51) Int. Cl.

| | | |
|---|---|---|
| *C07K 16/36* | (2006.01) | |
| *C07K 16/30* | (2006.01) | |
| *A61P 35/00* | (2006.01) | |
| *G01N 33/50* | (2006.01) | |
| *G01N 33/80* | (2006.01) | |
| *G01N 33/569* | (2006.01) | |

(52) U.S. Cl.
CPC .......... *C07K 16/3061* (2013.01); *A61P 35/00* (2018.01); *G01N 33/5094* (2013.01); *G01N 33/56966* (2013.01); *G01N 33/80* (2013.01); *C07K 2317/24* (2013.01); *C07K 2317/33* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 5,530,101 A | * | 6/1996 | Queen | C07K 16/00 424/133.1 |
| 2004/0180409 A1 | * | 9/2004 | McVicar | C07H 21/04 435/69.1 |
| 2008/0131423 A1 | * | 6/2008 | Mori | C07K 16/2803 424/130.1 |

FOREIGN PATENT DOCUMENTS

EP   2680875 A1  *  1/2014

OTHER PUBLICATIONS

Janeway et al., Immunobiology, 3rd edition, Garland Publications, 1997, pp. 3:1-3:11.*
Gattis et al., J Biol Chem. May 12, 2006;281(19):13396-403. Epub Feb. 27, 2006.*
Ferrer-Acosta et al., J Infect Dis Ther. Aug. 2014;2(4). pii: 149. doi: 10.4172/2332-0877.1000149. Epub Jun. 24, 2014.*
Kipriyanov et al., Mol Biotechnol. Jan. 2004;26(1):39-60.*

* cited by examiner

*Primary Examiner* — Michael Szperka
(74) *Attorney, Agent, or Firm* — Hoglund & Pamias, PSC; Roberto J. Rios

(57) ABSTRACT

A monoclonal antibody against human (a69) and mouse clones Triggering Receptor and (Clones Expressed in Myeloid TREM) cells-like transcript-1 or TLT-1 is provided. This antibody also identifies TLT-1 on platelets by flow cytometry, in western blots, by immunofluorescence, ELISA and immunoprecipitation giving it immediate use as a diagnostic tool for research and blood marker and/or treatment for diseases such as disseminated intravascular coagulation. The Antibody can also be used as intervention for any diseases that has or may have a TLT-1 component such as Disseminated Intravascular Coagulation (DIC), Cardiovascular disease (CVD) and cancers and should overcome the problem of blocking platelet function that leads to a bleeding diathesis.

11 Claims, 11 Drawing Sheets

Specification includes a Sequence Listing.

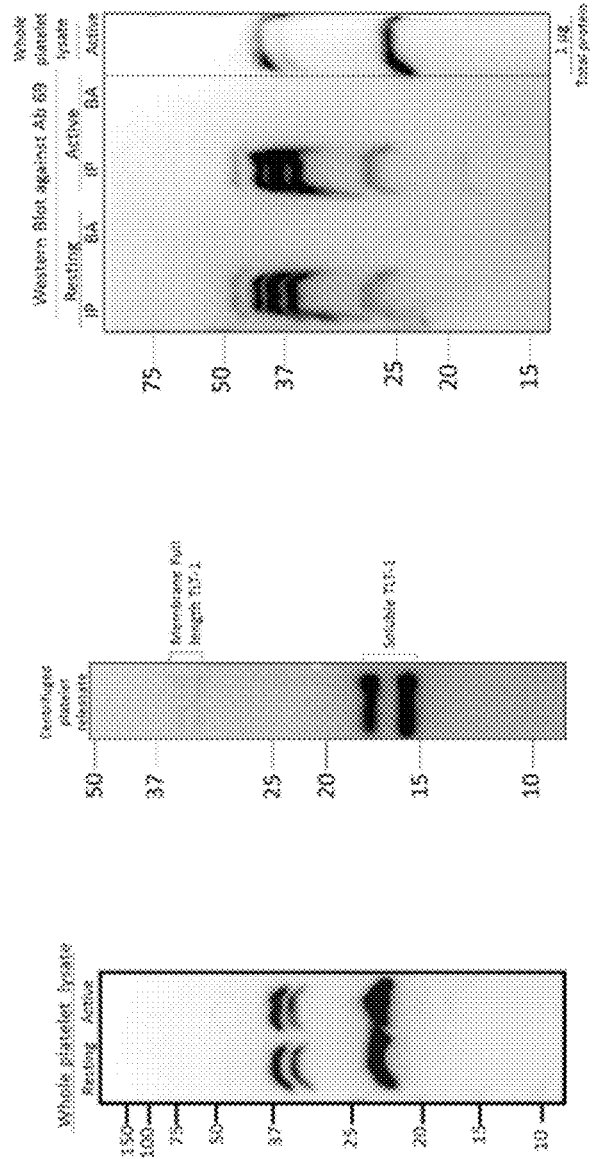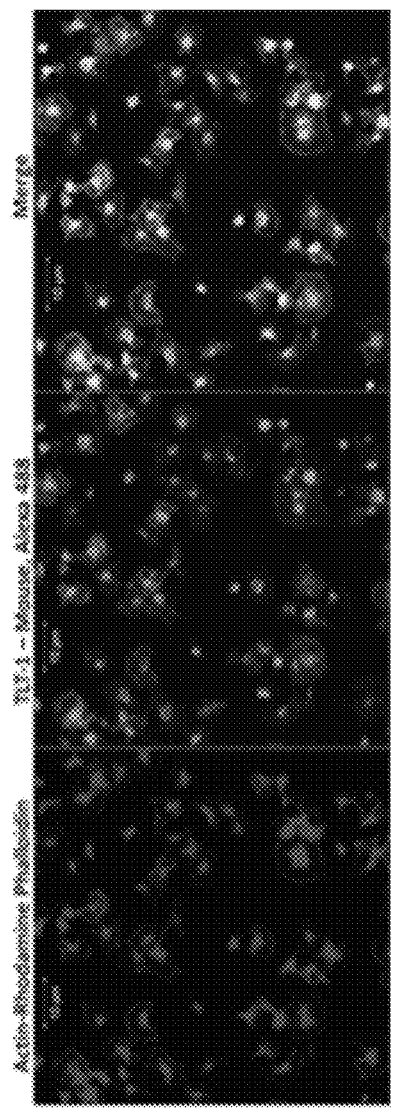
Figure 6A
Figure 6B
Figure 6C
Figure 6D

ANTI-TLT-1 ANTIBODY AND USES THEREOF

GOVERNMENT INTEREST

The claimed invention was made with U.S. Government support under grant number HL909033 awarded by the National Institutes of Health (NIH). The government has certain rights in this invention.

SEQUENCE LISTING

The instant application contains a Sequence Listing which has been filed electronically in ASCII format and is hereby incorporated by reference in its entirety. Said ASCII copy, created on Nov. 7, 2019, is named UPR-14230_ST25.txt and is 3,213 bytes in size.

BACKGROUND OF THE INVENTION

Platelets have a crucial role in vasculature maintenance of tumors besides their well-known role in hemostasis. Tumors grow and become metastatic at the expense of platelet activation to build their own unstable vascularization. Experiments where solid tumors injected to mice were platelet-depleted, reveal the development of hemorrhages specifically at the tumor site. These investigations demonstrated the importance of platelets in the maintenance of tumor vasculature stability. Tumors are well-known sites of angiogenesis and inflammation, and platelets are key mediators in both of these events, thus it is important to decipher the cellular crosstalk between platelets and endothelial cells to further develop effective anti-tumor treatments. So far, we know that platelets are important reservoirs of pro- and anti-angiogenic molecules and available anti-cancer treatment has been developed from the manipulation of these molecules in the blood, such as anti-VEGF antibodies. The use of anti-platelet molecules, such as cyclooxygenase (COX2) inhibitor aspirin and the P2Y12 receptor inhibitor ticagrelor, have been shown to provide benefits in cancer patients and in mouse models, respectively. Therefore, the identification of molecules that inhibit platelet aggregation could provide therapeutic potential.

We previously reported the TREM-Like transcript-1 protein (TLT-1) which is a 37 kDa transmembrane protein that is highly expressed in platelets and megakaryocytes. TLT-1 has three reported isoforms in platelets: TLT-1 full length (TLT-1), soluble TLT-1 (sTLT-1) and TLT-1 splice variant (TLT-1sv). After platelet activation these cells release a soluble extracellular fragment of TLT-1 (sTLT-1) that is detected in the serum but not in plasma of healthy mice or humans. Interestingly, TLT-1 is the platelet's fourth most abundant molecule in the platelet releasate. Further studies on this protein revealed that it has a role in hemostasis, as TLT-1 knockout mice showed predisposition to hemorrhage associated with a localized inflammatory lesion and had significantly longer tail bleeding times than normal mice. In addition, blockade of TLT-1 with a single chain antibody prevented thrombin-induced platelet aggregation. Morales et al (2009) showed how recombinant sTLT-1 enhanced platelet-endothelial cell adherence, suggesting that sTLT-1 could mediate hemostasis by enhancing actin polymerization in platelets and resulting in increased platelet aggregation and adherence to the endothelium. Interestingly, elevated levels of sTLT-1 are associated with both a role for TLT-1 in disease and the presence of disseminated intravascular coagulation (DIC). Cancer is one of a handful of diseases that are associated with disseminated intravascular coagulation (DIC). We have subsequently demonstrated in a nude mouse model, using sTLT-1 as a measure of DIC (because it correlates better than D-Dimers), that sTLT-1 levels are higher in mice with larger tumors than those with smaller tumors, suggesting a role for TLT-1/sTLT-1 in cancer progression.

Considering the therapeutic relevance of the released platelet-factors in tumor vasculature, the present invention demonstrates the signaling mechanisms of sTLT-1 release in platelets and a novel direct crosstalk between sTLT-1 and endothelial cells that leads to an increase in endothelial cell actin polymerization, the generation of pro-angiogenic features, and proangiogenic cytokine release in endothelial cells. Accordingly, the present invention proposes a new potential role of TLT-1 in the mediation of angiogenesis and a specific ant1-TLT-1 antibody that interacts with a CDR3 loop of TLT-1.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIGS. 6A-6E show that Antibody 69 can be used for TLT-1 detection by Western blot and immunofluorescence in human platelets.

DETAILED DESCRIPTION OF THE INVENTION

Materials and Methods

Platelet Isolation

Figure 1:
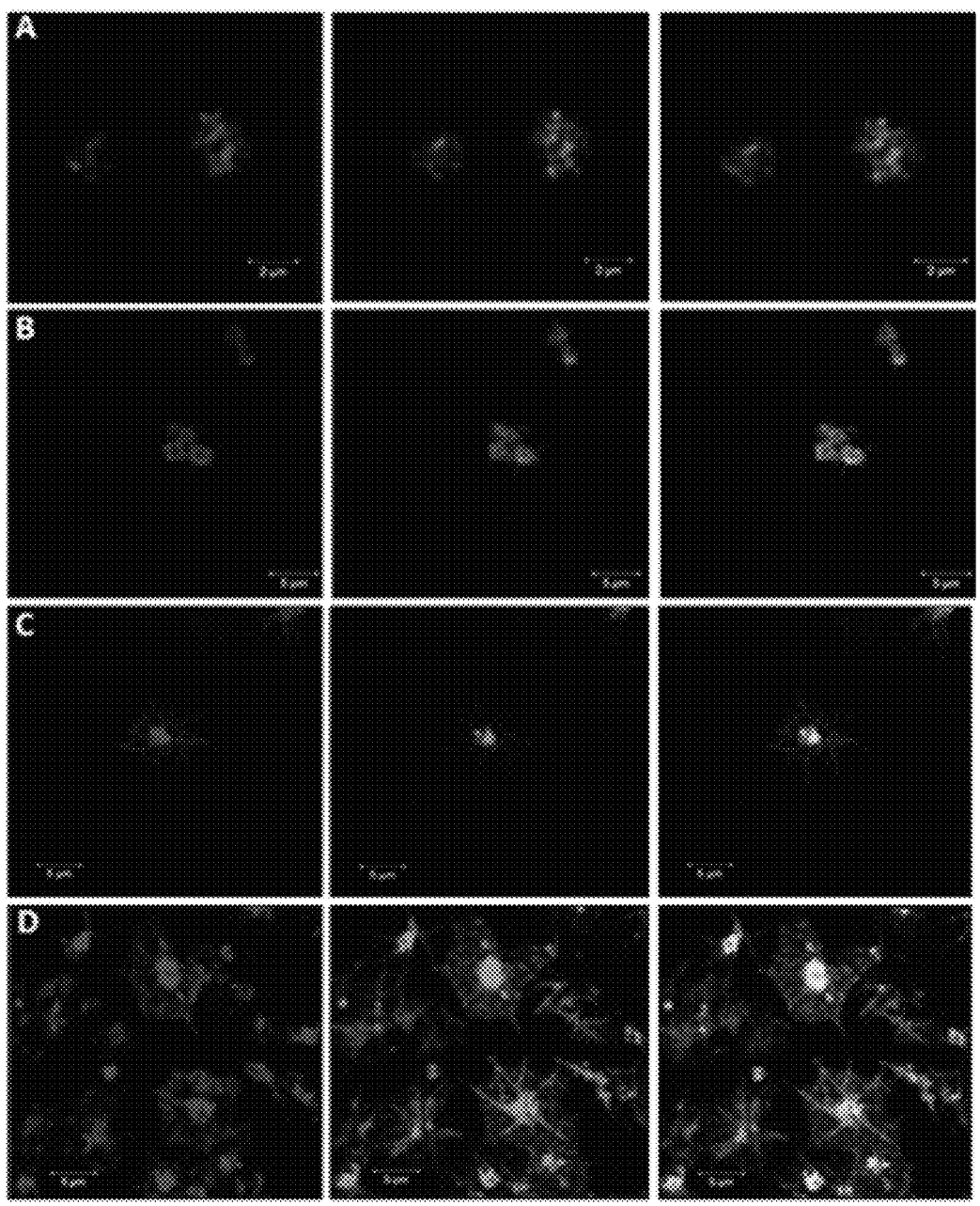
FIG. 1 shows the distribution of TLT-1 and P-selectin containing granules in human platelets.

The University of Puerto Rico, Rio Piedras Campus approved the study, and volunteer blood donors were provided verbal and written informed consent before enrollment. Platelets isolation protocol was adapted from a known method. Blood was obtained by venipuncture from healthy volunteers who had not taken any anti-inflammatory drugs for the previous 7 days.

30 mL of blood were drawn into polypropylene syringes containing one-sixth volume of Acid citrate dextran and centrifuged 20 min at 70×g in an angled-rotor centrifuge at 25° C. Platelet rich plasma (PRP) supernatant was removed and added 10% Acid Citrate Dextrose, 0.5 µM prostaglandin 12 ($PGI_2$) and 0.02 U/mL of apyrase. PRP was centrifuged at 3,000×g, 5 min, 25° C. Supernatant was removed and platelet pellet was washed with gentle resuspension twice using 1 mL of Tyrode's buffer (10 mM Hepes, 0.5 mM $MgCl_2$, 130 mM NaCl, 4 mM KCl, 1 mM $CaCl_2$, and 5 mM glucose, pH 7.4) supplemented with 0.5 µM prostaglandin and 0.02 U/mL of apyrase. In every wash cells were centrifuged at 2,500×g, 4 min at 25° C. Cells were counted and $1\times10^8$ total platelets per sample were used to perform cytospin. These cells were resuspended in Tyrode's buffer in a final volume of 250 µL. Cells were fixed by directly adding 200 µL of Cytofix (BD Biociences Cytofix/Permwash kit, cat no. 554714) to the 250 µL of platelets in the tube and incubating for 20 min at 25° C.

Cytospin Procedure

Fixed platelets were added to small coverslips (No. 1 Glass coverslip 12 mm) previously incubated 10 min. with a polylysine solution (0.1% w/v), rinsed with ddH20 and laid on a 12 well cell culture plate. To bind platelets to coverslips, cells were centrifuged at 240×g, 5 min, 25° C., on a tabletop centrifuge with plate adaptors. Supernatant was removed from the wells and cells in coverslips were gently rinsed twice with 1 mL PBS and blocked/permeabilized with 1 mL of Cytoperm for 20 min at 25° C. The desired antibody (1:200) was diluted in Cytoperm and added to the coverslip for 1 hr at 25° C. Primary antibody was removed and coverslip was washed with 1 mL PBS 3 times. Secondary fluorescent antibodies (1:500), were dissolved in Permwash blocking solution and incubated 30 min. at 25° C. Secondary antibodies were removed and coverslips washed 5 times with 1 mL PBS. Microscope glass slides were added fluorescence mounting media and coverslips with stained cells were laid facing the mounting media and dried for further analysis by confocal imaging.

Image Acquisition and Analysis of Confocal Images

Confocal images of platelets (FIGS. 1-3) were acquired using a ZEISS® LSM-5 Pascal scanning confocal microscope. For the excitation of Alexa Fluor 488, an argon laser was used, and emission was detected using BP 505-530 filter. For excitation of rhodamine phalloidin, ALEXA FLUOR® 555 and 568, a helium-neon laser was used and emission was detected using LP 560 filter. The ZEISS® LSM5 PASCAL Image software, version 3.2 was used to create the final images. To analyze and quantify fluorescence on FIG. 3, the Carl Zeiss imaging program ZENBlue was used. To obtain unbiased counting, cells were scored without knowledge of their prior treatment. On FIGS. 5-7, HUVECs were imaged using a ZEISS® LSM 510 META on an Axiovision Z1 microscope. On FIG. 4, the quantification of rhodamine phalloidin on HUVECs was performed using the Metamorph program.

Immunofluorescence Staining

After cytospin, fixed platelets were stained with the following unconjugated antibodies: Mouse Anti-human P-selectin and Rat anti human-TLT-1, Rabbit anti VEGF Ab-1 and Rabbit Anti-Endostatin. The secondary antibodies used were: anti-Rabbit Rhodamine X, Exc.570 nm, anti-Mouse Alexa 488, anti-Mouse Alexa 568, and anti-Rat FITC. Actin staining was performed using rhodamine phalloidin (1:1000, MOLECULAR PROBES®) or phalloidin 647 (1:200, MOLECULAR PROBES®), and nuclear staining was made using DAPI.

G-LISA Small GTPase Activity Assays

To measure Cdc42 activation on HUVECs upon addition of sTLT-1, a small GTPase activity assay (G-LISA, Cytoskeleton, Inc. cat no. BK127) was used. HUVECs ($1\times10^6$ cells, passing numbers 3-5) were grown in vascular cell basal media (ATCC®) supplemented with endothelial cell growth kit BBE (ATCC®, cat no. PCS-100-040) containing bovine brain extract (BBE, 0.2%), rh EGF (5 ng/mL), L-glutamine (10 mM), heparin sulfate (0.75 Units/mL), hydrocortisone (1 µg/mL), ascorbic acid (50 µg/mL), ATCC® fetal bovine serum (FBS, 2%). Cells were then starved overnight in 1% FBS and next day these were changed to serum-free media and left overnight. Cells were grown up to 70% confluency, media was removed, and cells were added 10 mL serum-free media with sTLT-1 (5.5 ng/µL) for 30 min. Media was removed, cells were washed with 10 mL cold PBS twice and added 700 µL lysis buffer. Cell lysates of untreated and sTLT-1 treated HUVECs were prepared by cell-scraping and centrifugation, following Cdc42 G-LISA kit instructions. Concentration of lysates was determined and equal amounts of protein (0.5 mg/mL) were added to the Cdc42 G-LISA 96-well plate. Activated Cdc42 signal was detected by measuring absorbance at 490 nm in a 96-well plate reader (TECAN® Infinite M200 Pro Plate Reader).

Tube Formation Assays

To test the effect of sTLT-1 on human endothelial cell tube formation, Human umbilical vein endothelial cells (HUVECs human, pooled, ATCC®, cat no. PCS 100-013) treated with sTLT-1. To perform these studies, HUVECs were grown in MATRIGEL® growth factor reduced basement membrane matrix (Corning) using the thin coat method. In this method, a 1:5 ratio of ice cold Matrigel to Matrigel buffer (10 mM Tris Base, 0.7% w/v NaCl, pH 8) was prepared. On a 48 well plate, 200 µL of this mixture were added per well and plates were left to polymerize at 37° C. for 1:30 hrs. In a final volume of 250 µL vascular cell basal media supplemented with BBE kit (ATCC®), HUVECs ($1.25\times10^5$ cells, passing number 2-5) were: a) untreated, b) added 25 ng/µL human recombinant sTLT-1, c) added 25 ng/µL human recombinant sTLT-1 together with the TLT-1 single-chain blocking antibody C10. After 26 hrs of incubation at 37° C., 95% air, 5% $CO_2$, cells were photographed and analyzed.

Cytokine Release Assays

The Cytometric Beads Assay-Human Inflammatory Cytokine kit was used to quantify eight cytokines from supernatants of HUVECs that were added sTLT-1 (25 ng/µL), untreated, or added sTLT1 (25 ng/µL)+C10 (120 ng/µL) in the tube formation assays after 26 hrs. This kit was used to measure the following cytokines: Interleukin-8 (IL-8), Interleukin-1β (IL-1β), Interleukin-6 (IL-6), Interleukin-10 (IL-10), Tumor Necrosis Factor (TNF), and Interleukin-12p70 (IL-12). Fifty microliters of cell supernatant were used for this kit, following the product's manual instructions for tissue culture supernatant samples and samples were read by flow cytometry (ACCURI® C6 four-color Flow Cytometer).

Immunoprecipitation

To test the novel Antibody (a69) capacity to immunoprecipitate TLT-1, $3.13\times10^8$ total platelets in 900 µL Tyrode's buffer were activated for 10 min with 0.001 U/mL thrombin at 37° C. Resting platelets had the same treatment without thrombin. Platelet lysate was made by adding 100 uL of 10×

Chaps lysis buffer supplemented with 10× protease inhibitor cocktail, 10 mM PMSF and 10 mM Sodium Orthovanadate when added to the platelets. Platelets were resuspended and centrifuged at 4° C., at 14,000 rpm for 10 min. 500 µL of resting and activated platelets were incubated with either 100 µL of Antibody (a69) or 100 µL buffer. The Beads Alone control was also made with 500 µL of each lysate, 25 µL of a 1:1 mix of Protein A and Protein G antibody affinity beads was used to incubate with each sample. Immunoprecipitation was made with rotation for 1 hour at 4° C. and incubation with beads was also made with rotation for 1 hour at 4° C. Beads were washed 4 times with 400 µL buffer with centrifugation 1 min at 5,000×g at 4° C. Beads were resuspended with 25 µL of 2×SDS Laemmli loading buffer and supernatant was run on an SDS PAGE and western blotted against TLT-1 using 1:500 Antibody a69.

Western Blots

Figure 3A:
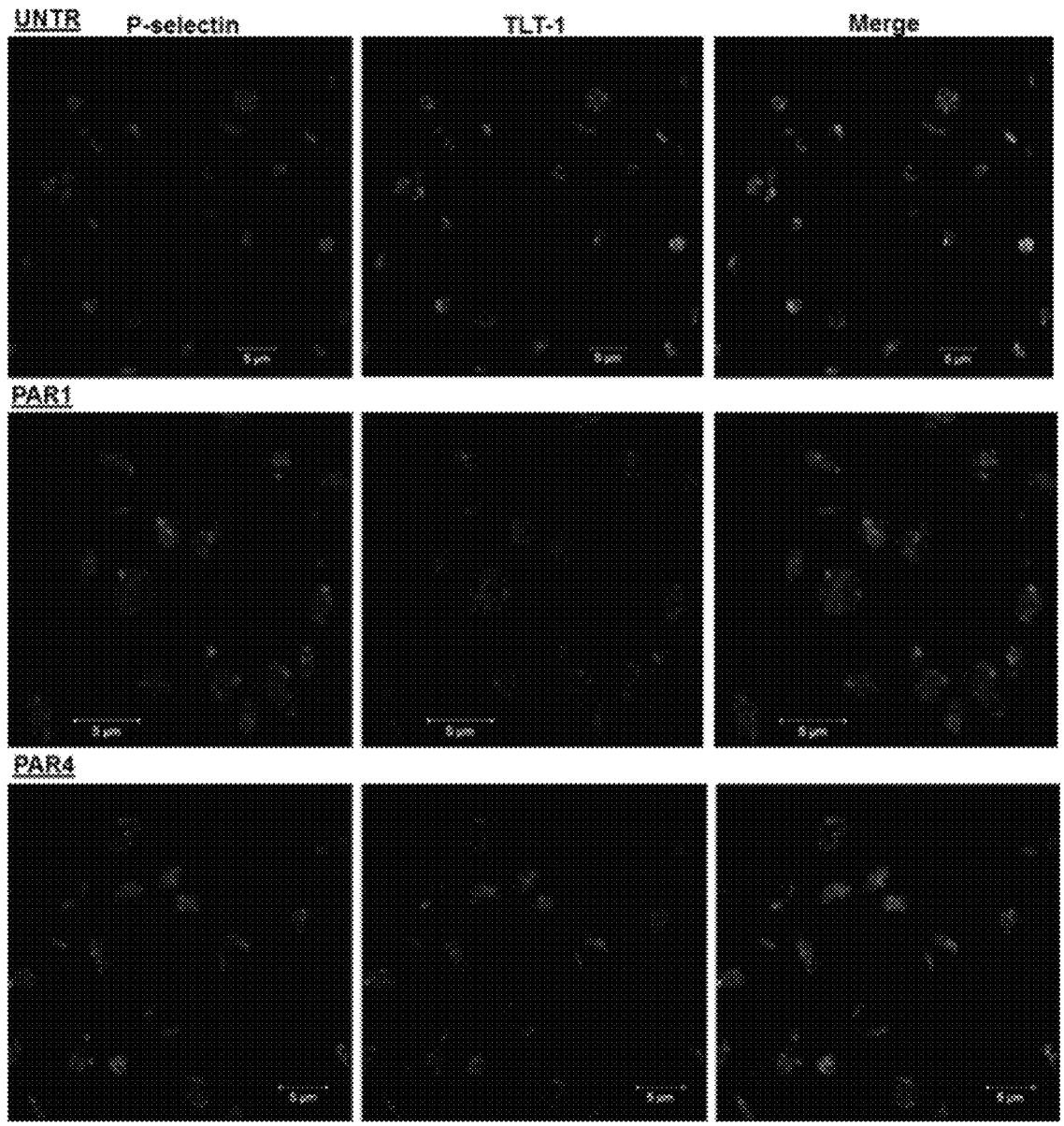
FIGS. 3A and 3B show the effects of PAR-1 and PAR-4 agonists on sTLT-1 distribution and release in human platelets.
Figure 3B:
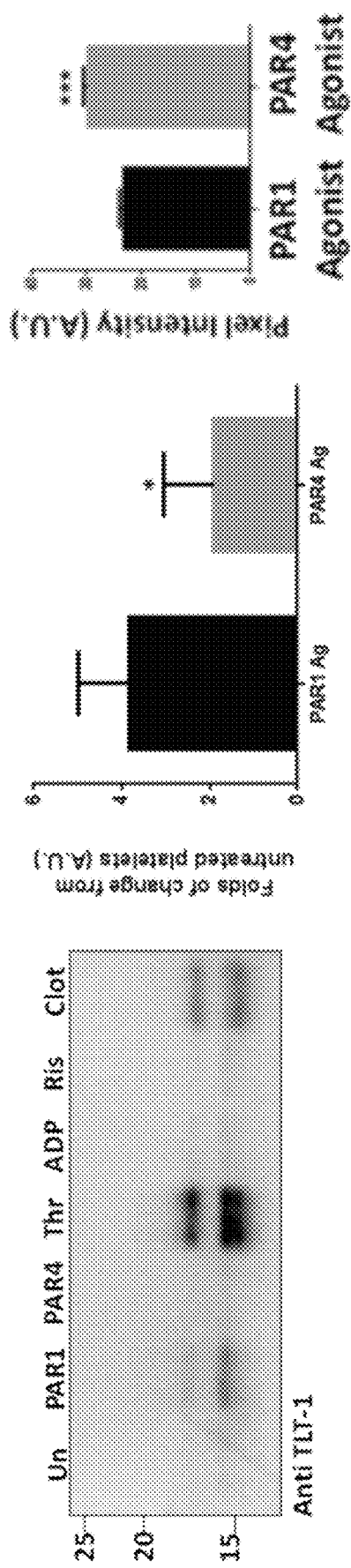
Figure 4:
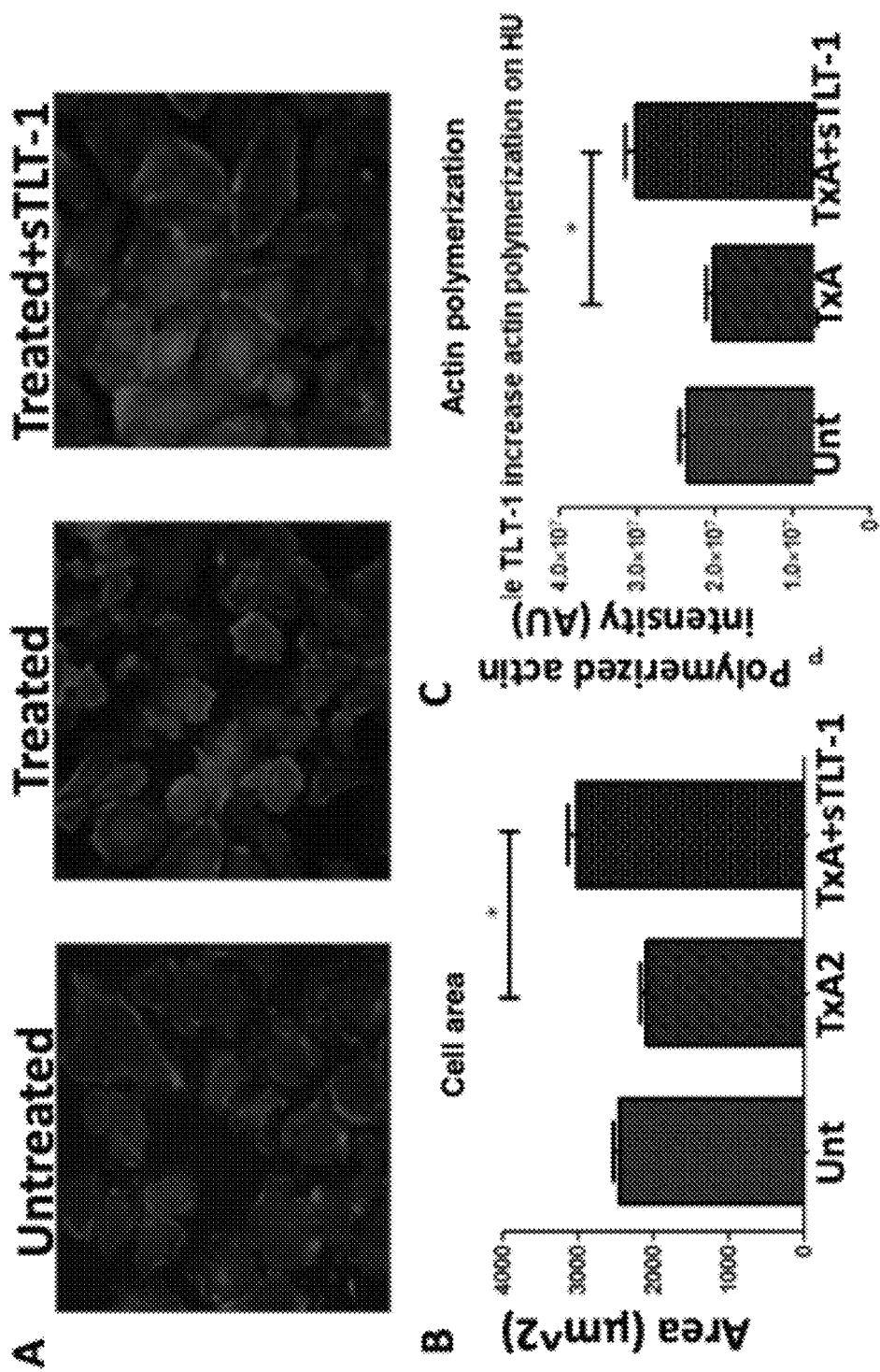
FIG. 4 shows that soluble TLT-1 increases actin polymerization and cell area in HUVECs.

In FIG. 3B, to detect the released soluble TLT1 by Western blot, human platelets ($4.7 \times 10^7$ total platelets) were isolated, washed and added: PAR1 agonist, TFFLR (8 µM), PAR4 agonist, AYPGK (10 µM), or no treatment in a volume of 125 µL, for 10 min at 37° C. To compare sTLT-1 platelet release upon addition of other known activators, platelets were added: thrombin (0.01 U/µL), adenosine diphosphate (ADP, 5 µM) and ristocetin (Ris, 0.5 mg/mL). Platelets were centrifuged, supernatant was removed and 15 µL were run and analyzed by Western blot against TLT-1 (Goat anti human TLT-1). In addition, 5 µL of a human platelet clot releasate were used as a positive control.

In FIG. 6A, to detect TLT-1 from human platelets using Antibody a69, protein lysate preparation was made as in the immunoprecipitation protocol. 15 µg total protein of cell lysates was loaded on a 12% SDS PAGE. Membranes were blocked with 5% milk and incubated with 1:500 Mouse Anti-human TLT-1 Antibody a69.

In FIG. 6B, platelet releasate from isolated, clotted platelets ($1.1 \times 10^5$ platelets/µL) was obtained. 1 mL of releasate in Tyrode's buffer was spun down 10 min. at 14,000×g. 25 µL of the centrifuged releasates were resuspended in 6× loading buffer with 5% β-Me, heated 5 min. at 95° C. and loaded on a 15% Acrylamide gel. Membranes were blocked with 5% milk and incubated with 1:1000 Mouse Anti-TLT-1 Antibody a69.

Statistical Analyses

Analyses were performed using the Prism software (version 5.01, GRAPHPAD® Software). Figure bars in graphs are expressed as means±SD. Statistical significance was evaluated for all analyses in with a paired, 2-tailed Student's T-test and a p value <0.05 was considered statistically significant.

Results

Differential Distribution of TLT-1 in Resting and Activated Human Platelets

To examine the distribution of TLT-1 in human platelets, its dispersal pattern was compared to that of the well-known α-granule protein, P-selectin. Platelets in resting and activated state were isolated, washed, incubated 1 hour at 37° C., fixed in suspension and cytospun. Activated platelets were added thrombin (0.01 U/µL) for 10 min or spread on glass for 3 and 15 minutes. Immunofluorescence against P-selectin and TLT-1 was performed (FIG. 1). On FIG. 1A, a close look at the resting platelets show a differential distribution of TLT-1 on α-granules, as some granules seem to contain TLT-1 only (green), others are yellow, colocalizing with P-selectin, while others only have P-selectin (red). Localization of TLT-1 and P-selectin in isolated, resting human platelets processed by the cytospin method, was done by using double staining immunofluorescence microscopy. Platelets were labeled with antibodies against P-selectin (Alexa 568, red) and TLT-1 (FITC, green). These results led us to further examine the distribution of TLT-1 upon platelet activation in human platelets. When platelets are activated with thrombin (FIG. 1B), these cells shrink and develop filopodia. Localization of these two proteins was also studied in activated platelets with thrombin for 10 minutes. TLT-1 distribution upon platelet activation revealed that part of the pool of TLT-1 in the platelet colocalizes with P-selectin, in the outermost area of the platelet around the marginal microtubules, while another pool remains around the central area of the platelet, in the granulomere. When platelets are spread in glass there is also differential distribution of TLT-1 in a time-dependent manner (FIGS. 1C-D). Panel C and D show the distribution of TLT-1 and P-selectin after platelets were spread in glass for 3 and 15 minutes, respectively. After 3 minutes of platelet spreading in glass, TLT-1 and P-selectin colocalize in the granulomere and spread throughout the platelet's filopodia (FIG. 1C). After 15 minutes, both proteins still colocalize in the granulomere, yet they disperse differentially through the platelet, as TLT-1 distributes throughout the filopodia and plasma membrane, while P-selectin remains mostly distributed around the plasma membrane (FIG. 1D).

Figure 2:
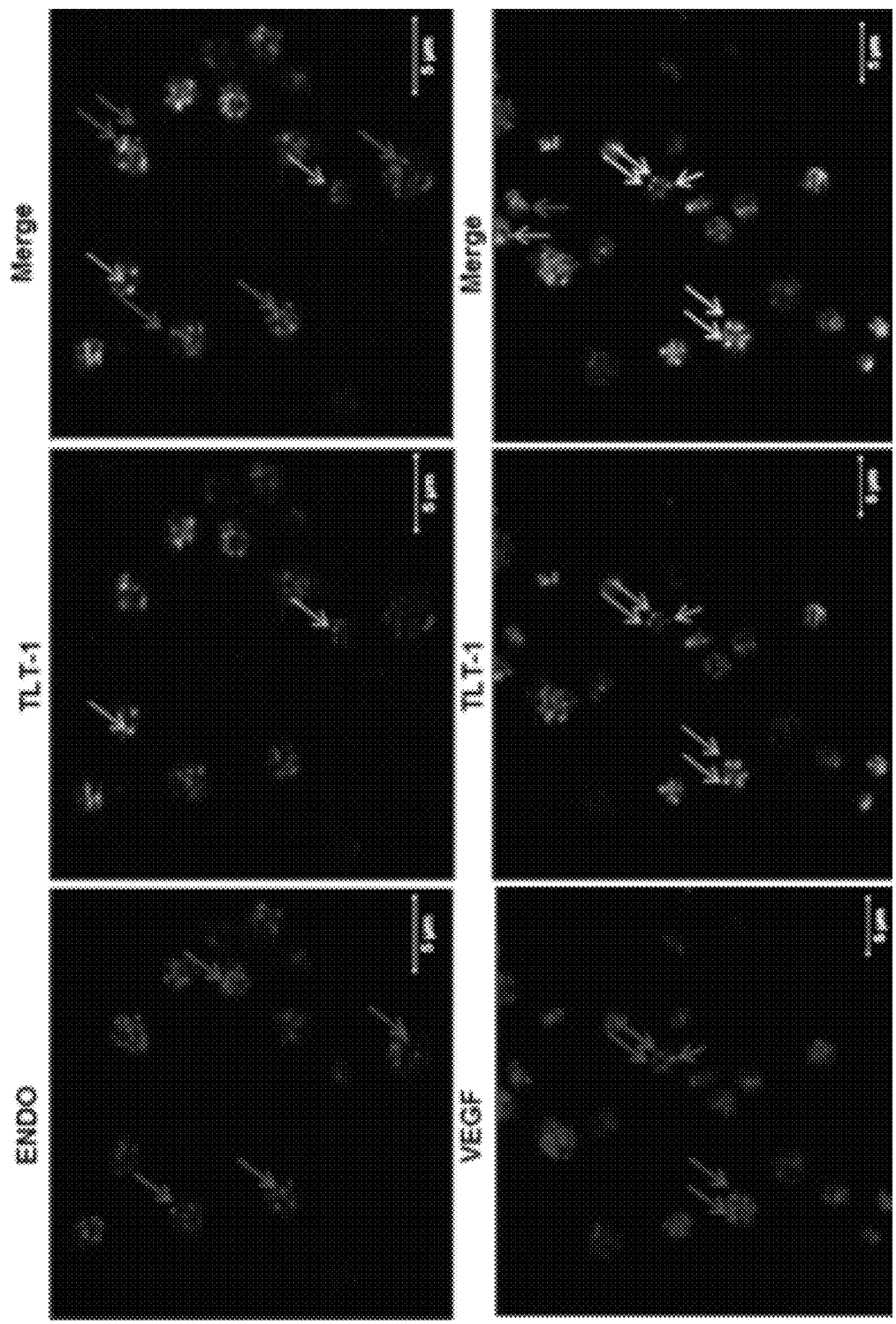
FIG. 2 shows that TLT-1 colocalizes with VEGF positive α-granules.

Colocalization of TLT-1 with Vascular Endothelial Growth Factor (VEGF) Positive α-Granules Studies have shown that α-granules can have different cargo and these granules can each be specifically released depending on the signaling ligands that act upon platelets. More specifically, the study focused on the differential release of VEGF and endostatin (ENDO)-containing α-granules upon PAR-1 and PAR-4 receptor signaling in platelets, respectively. After our initial observation of TLT-1 differential distribution in α-granules, a qualitative analysis of TLT-1 colocalization with VEGF and ENDO in human platelets was made. Human platelets were isolated, incubated at 37° C. for 1 hour, fixed, adhered to coverslip by cytospin and stained against TLT-1 and ENDO (FIG. 2, upper panel) or TLT-1 and VEGF (FIG. 2, lower panel). Human platelets were isolated, incubated at 37° C. for 1 hour, fixed, and stained for endostatin (red, upper panel), VEGF (red, lower panel) and TLT-1 (green). Red arrows point VEGF or ENDO positive granules, green arrows show TLT-1 positive granules and yellow arrows show granule colocalization.

Our results show a greater amount of TLT-1-containing granules colocalizing with VEGF positive granules when compared to ENDO positive granules. These results indicate that TLT-1, as a protein contained in VEGF-positive granules, could be differentially released upon PAR signaling in platelets.

Effects of PAR-1 and PAR-4 Agonists on TLT-1 Release from α-Granules in Platelets To test that TLT-1 could be differentially released upon PAR-1 versus PAR-4 receptor signaling, human platelets ($1 \times 10^7$ total) were isolated, washed, and added either PAR-1 agonist TFFLR (8 µM), PAR-4 agonist AYPGK (10 µM) or no treatment, for 10 min at 37° C. Cells were fixed, adhered by cytospin, and stained for P-selectin and TLT-1 (FIG. 3A). On the top panel, human platelets ($1 \times 10^7$ total) were isolated and washed. Cells were fixed, cytospin, and stained for P-selectin (red, Ms Alexa 568) and TLT-1 (green, Rat FITC). On middle and bottom panels, cells were added either PAR1 agonist TFFLR (8 µM) or PAR4 agonist AYPGK (10 µM) for 10 min at 37° C. TLT-1 fluorescence was quantified in both conditions for 156 platelets each, T test, p=0.0001. A significant decrease in TLT-1 signal was observed upon the addition of PAR-1 agonist (FIG. 3A, middle panel) when compared to untreated (FIG. 3A, upper panel) and to PAR-4 agonist treated cells (FIG. 3A, lower panel). TLT-1 fluorescence in PAR-1 and PAR-4 agonist-treated platelets was quantified (156 platelets for each condition) and a Student's, T test, p=0.0001 showed significantly lower fluorescence in the PAR-treated platelets. These results show that TLT-1 can be differentially released from platelets upon PAR-1 and PAR-4 signaling.

TLT-1 extracellular fragment (~17 kDa) can be either cleaved or released from α-granules upon platelet activation. Thus, we submit that this fragment would be found in greater amounts on platelet releasates of platelets exposed to PAR-1 agonist versus PAR-4 agonist or untreated platelets. To test this, human platelets ($4.7 \times 10^7$ total platelets) were isolated, washed, and resuspended in Tyrode's buffer with either of the following agonists: 8 μM PAR1 agonist TFLLR, 10 μM PAR4 agonist AYPGK; or platelet activators for comparison: 0.01 U/μL thrombin (Thr), 5 μM Adenosine diphosphate (ADP), 0.5 mg/mL ristocetin (Ris); or untreated (Unt). After incubation with these treatments for 10 min at 37° C., releaseate was obtained by centrifugation of platelets (3,000×g, 5 min) and centrifugation of supernatant (3,000× g, 5 min). Same amounts of releasates (10 μL) were loaded on an acrylamide gel and immunoblotted against human TLT-1. A clot releaseate, besides thrombin, was used as a positive control for sTLT-1 release (FIG. 3B). On the left panel, Human platelets ($4.7 \times 10^7$ total) were isolated, washed and added: PAR-1 agonist TFFLR (8 μM, PAR1 lane), PAR-4 agonist AYPGK (10 μM, PAR4 lane), platelet activators for comparison: 0.01 U/μL thrombin (Thr), 5 μM Adenosine diphosphate (ADP), 0.5 mg/mL ristocetin (Ris); or untreated (Unt). Platelets were exposed to the different conditions at 37° C. for 10 min, centrifuged, and equal amounts of supernatants were run and analyzed by western blot against TLT-1. Thrombin treatment and the clot supernatant (Clot lane) were used as positive controls of sTLT-1 release from platelets. On the right panel, Folds of change between PAR1 agonist and PAR4 agonist treated platelets from the untreated platelets control (right panel), were calculated by densitometry. These are representative of four independent experiments, Student's T-test p<0.05. Folds of change between untreated platelets and PAR-1/PAR-4 agonist-treated platelets, were calculated by densitometry (FIG. 3B, right panel). The densitometry is representative of four independent experiments, and a Student's T-test showed a p<0.05. These results show that soluble TLT-1 is increasingly released from platelets after PAR-1 agonist exposure compared to PAR-4 agonist, ADP, the collagen receptor agonist ristocetin or untreated platelets. Positive controls on these experiments, thrombin and platelet clot, showed the highest amount of sTLT-1 on releasates, as previously published. Altogether, these results confirm that soluble TLT-1 is differentially released from platelets upon PAR-1 agonist exposure compared to PAR-4 agonist.

Soluble TLT-1 Directly Increases Area and Actin Polymerization on HUVECs

Based on the previous results, we hypothesize that the release of sTLT-1 from platelets, specifically from VEGF containing α-granules, could exert a direct effect on cells such as endothelial cells (which are highly responsive to VEGF), without the need of other platelet mediators or platelet-endothelial cell interactions. To test this hypothesis, we used an experimental model based on previous studies from our laboratory in which thromboxane A2 ($TxA_2$) was used as a cell activator. TLT-1 has been shown to have an important role inhibiting $TxA_2$-mediated platelet activation. $TxA_2$ is also an endothelial cell activator, causing endothelial cell withdrawal and shrinkage upon its addition. Thus, we decided to test whether sTLT-1 alone could have an important role inhibiting $TxA_2$-mediated endothelial cell activation. Thus, by adding $TxA_2$ in the presence and absence of sTLT-1 we could measure if there are changes in endothelial cell withdrawal and shrinkage and test our hypothesis of sTLT-1 exerting a direct effect on endothelial cells. To test this, HUVECs were added $TxA_2$ (75 nM) alone, $TxA_2$ (75 nM) plus sTLT-1 (100 μg/mL) or untreated. Samples were incubated at 37° C. for 30 min and cells were fixed and stained with rhodamine phalloidin (FIG. 4A). On the left panel, confocal microscopy of HUVECs grown in vitro stained with rhodamine phalloidin, untreated. On the middle panel, cells were added the platelet activator Thromboxane A (TxA2, 75 nM). In the right panel, cells treated with $TxA_2$ were also added recombinant soluble TLT-1 (sTLT-1) 100 μg/mL. All treatments were made for 30 min. at 37° C. Using the METAMORPH® software, cell area and actin polymerization were measured in at least 145 cells per condition in each of 3 experiments (FIG. 4B-C), p<0.05, student's T-test (paired, 2 tailed).

Our results showed that sTLT-1 alone can inhibit, $TxA_2$-induced endothelial cell shrinkage and promotes actin polymerization on these cells as well. With these results, we proved our hypothesis that sTLT-1 alone (without the need of other platelet molecules or interactions) can induce an effect on HUVECs.

Introduction of Antibody a69, a Novel TLT-1 Monoclonal Antibody

TLT-1 Antibody 69 is a monoclonal antibody that was generated by immunizing mice with human soluble TLT-1, which contains the extracellular domain that is conserved on all of the isoforms of TLT-1 in platelets. We have implemented several uses for this antibody, such as: Western blot, immunoprecipitation, immunofluorescence, flow cytometry and epitope blocking for in vitro studies (FIG. 6 A-D, FIGS. 7-9). To test the ability of TLT-1 Antibody a69 for Western blot, 15 μg of resting and thrombin-activated human platelet lysates (0.01 U/μL thrombin) were run on an SDS PAGE, transferred to a PVDF membrane. The membrane was subsequently blocked for 1 hour with 5% milk in tris buffered saline then 1 hour with antibody 69. Membrane was washed with tris buffered saline with tween then exposed with an anti-mouse HRP antibody for 1 hour. Membrane was then treated with ECL and image taken on the Chemidoc. Seen are the isoforms of human TLT-1. and incubated with Antibody a69. This antibody (1:500) was able to detect the human full length and short TLT-1 isoforms (FIG. 6B). To test its immunoprecipitation capacity, the same platelet lysates were incubated with TLT-1 Antibody a69 rotating at 4° C., 1 hr. and a Western blot against TLT-1 was performed to detect the protein. As observed in FIG. 6C, TLT-1 Antibody a69 could immunoprecipitate and 'enrich' several species of TLT-1 that cannot be detected only by western blot of whole lysate, showing its efficiency on this application. To test its use in immunofluorescence, isolated human platelets were spread in glass for 10 minutes and detection of TLT-1 using Antibody a69 (1:50) and anti-mouse Alexa 488 (TLT-1, green) as secondary antibody was made (FIG. 6D). To stain against actin, rhodamine phalloidin was used (red). The merge shows co-localization between TLT-1 and actin.

As shown in FIG. 6E, flow cytometry was performed on cells using Ab69 (pink), control IgG (blue) or unlabeled cells (red). Platelets were activated for 10 minutes with 10 mM ADP and washed in FAC buffer (1x PBS, 0.5% BSA, 0.5% Azide). Primary antibodies were allowed to be incubated with the platelets for 15 minutes, the platelets were washed with FACS buffer and the platelets were incubated with labeled secondary. Cells were washed and then run on the flow cytometry where we demonstrate the specific labeling of platelets using the TLT-1 antibody AB69. Accordingly, these results strongly indicate that the Antibody a69 interacts with the CDR3 loop of TLT-1.

This antibody showed strong presence of TLT-1 in the granulomere, where α-granules are stored, and throughout the platelet, detecting the membrane-bound protein with the extracellular domain. Finally, this antibody has also been shown useful to detect TLT-1 in platelets by flow cytometry. Thus, the versatility in uses of this antibody makes it an excellent tool for detection and determination of TLT-1 roles in humans.

TABLE 1

(Antibody a69 - Sequence Information)

| SEQ ID NO. | Description | SEQUENCE |
|---|---|---|
| 1 | Heavy Chain Variable Region - CDR1 | acccactggatgcag |
| 2 | Heavy Chain Variable Region - CDR2 | gctatttatcctggagatggta atactagatacactcagaatttcaag ggc |
| 3 | Heavy Chain Variable Region - CDR3 | tggggcgcagggaccacggtcaccgt ctcctca |
| 4 | Light Chain Variable Region - CDR1 | agggccagccaaagtcttagcaacaa cctacac |
| 5 | Light Chain Variable Region - CDR2 | gcttcccagtccatctct |
| 6 | Light Chain Variable Region - CDR3 | caacagagtaacagctggccgtacac gttcg |
| 7 | Heavy Chain Variable Region Framework Region - FWR1 | caggttcagctgcagcagtctgggc tgagctggcaagacctggggcttcag tgaagttgtcctgcaaggcttctggc tacaccttact |
| 8 | Heavy Chain Variable Region Framework Region - FWR2 | tgggtaaaacagaggcctggaca gggtctggaatggattggg |
| 9 | Heavy Chain Variable Region Framework Region - FWR3 | aaggccacattgactgcagatatat cctccagcaccgcctacatgcaact cagcagcttggcatctgaggactctgc ggtctattactgtgcaaga |
| 10 | Light Chain Variable Region Framework Region - FWR1 | gatattgtgctaactcagtctccag ccaccctgtctgtgactccagga gatagcgtcagtctttcctgc |
| 11 | Light Chain Variable Region Framework Region - FWR2 | tggtatcaacaaaaatcacatga gtctcctaggcttctcatcaattat |
| 12 | Light Chain Variable Region Framework Region - FWR3 | gggatccctccaggttcagtgg cagtggatcagggacagattt cactctccgtatcaacagtgtgg agactgaagattttggaatgtattt ctgt |

Soluble TLT-1 can be Endocytosed by Endothelial Cells

Figure 5A:
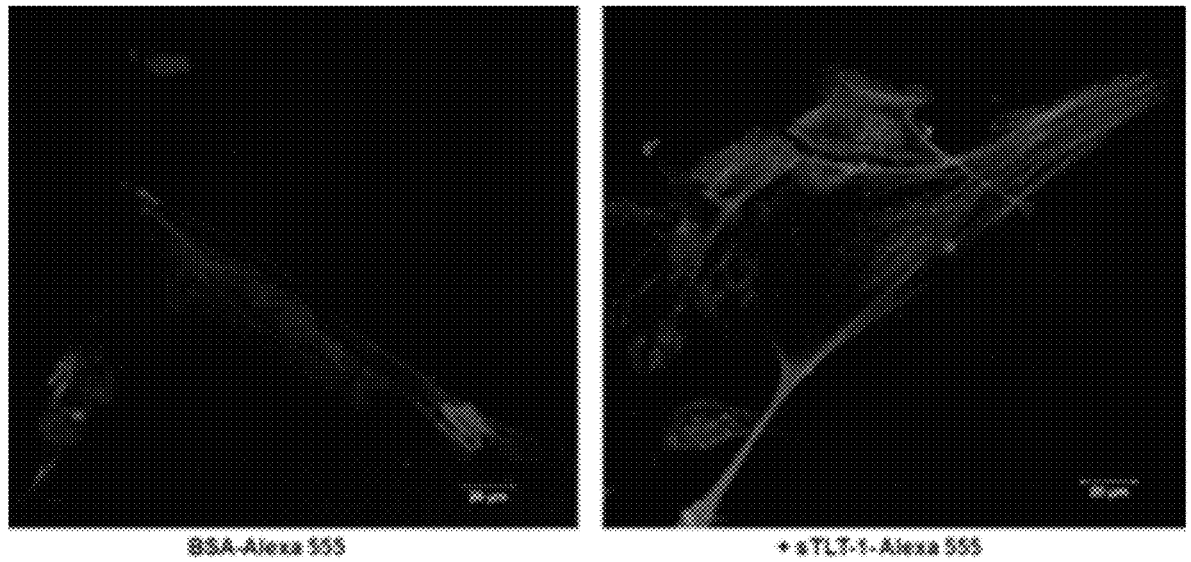
FIGS. 5A and 5B show that human soluble TLT-1 is endocytosed by HUVECs.
Figure 5B:
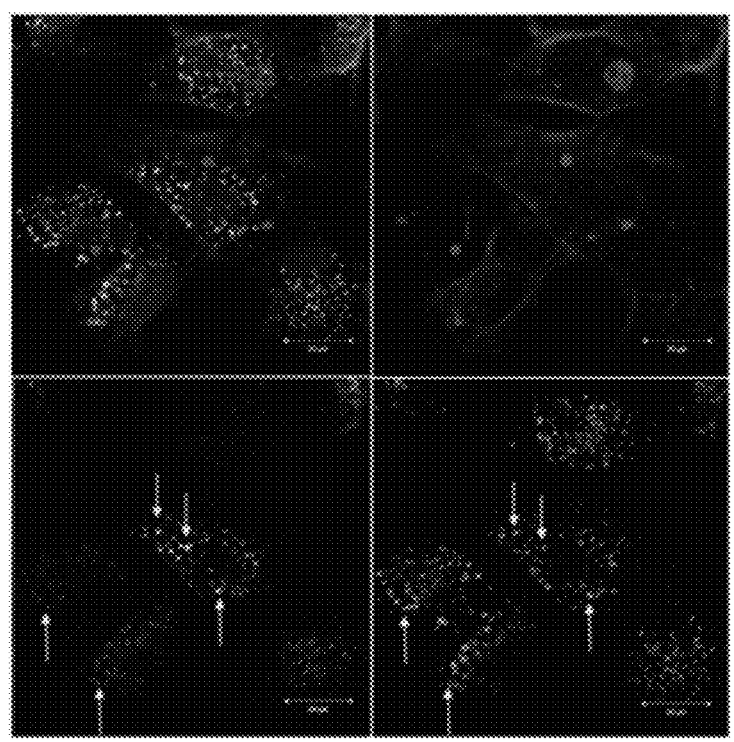

The results showing that sTLT1 had a direct effect on cell area and actin polymerization of HUVECs, prompted us to test whether this molecule could be internalized by endothelial cells, or if it remained on the cell surface. To test this, sTLT-1 labeled with Alexa 555 (1.8 µg/mL) was added to cultured HUVECs (3×10⁵ cells in a 6-well plate, over a glass coverslip) and incubated for 30 minutes at 37° C. As control, Alexa 555-labeled BSA (1.8 µg/mL) was incubated with HUVECs under the same conditions. Cells were washed 3 times with PBS, fixed, blocked, permeabilized with CYTOFIX/PERMWASH®, stained with phalloidin 647 (1:200, MOLECULAR PROBES®) and DAPI. Visualization by confocal microscopy showed that after 30 minutes, sTLT-1 was internalized by HUVECs compared to the BSA control (FIG. 5A). Time-dependent experiments showed that this molecule could be internalized in as soon as 5 minutes after incubation with HUVECs. To answer the question of whether this uptake could be through endocytosis, the same experiment was carried out and antibodies against early (clathrin, caveolin-1, Rab5, EEA-1) and late endosome (Rab 7, Rab11) markers were tested by immunofluorescence and analyzed using confocal microscopy. Colocalization of sTLT-1 Alexa 555 inside HUVECs with early endosome antigen-1 (EEA-1) was observed after 30 minutes of incubation (FIG. 5B). HUVECs were incubated with sTLT-1 Alexa 555 (orange, lower left panel) 30 min. at 37° C. Cells were fixed and stained against an early endosome marker protein EEA-1 (green, lower right panel). A merged image of sTLT-1 and EEA-1 (Upper right panel) shows a clear colocalization of these two proteins (arrows, lower panels). The other markers did not colocalize with sTLT-1 at this time point. These results show for the first time the recruitment of sTLT-1 by endothelial cells through endocytosis. Thus, these experiments demonstrate that sTLT-1 mediates a crosstalk between platelets and endothelial cells which could activate cell signaling cascades that lead to its presence in early endosomes.

Figure 7A:
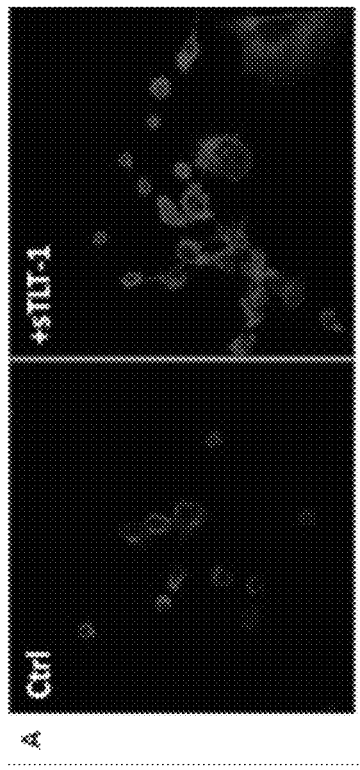
FIGS. 7A-7D show the effect of sTLT-1 in HUVECs filopodia formation and small Rho GTPase activation.
Figure 7B:
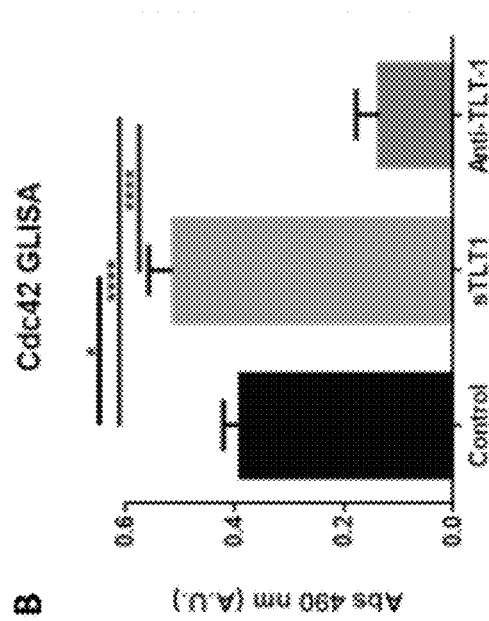
Figure 7C:
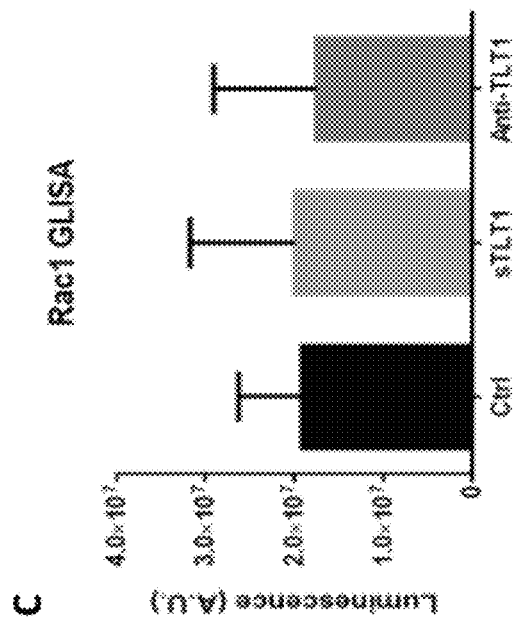
Figure 7D:
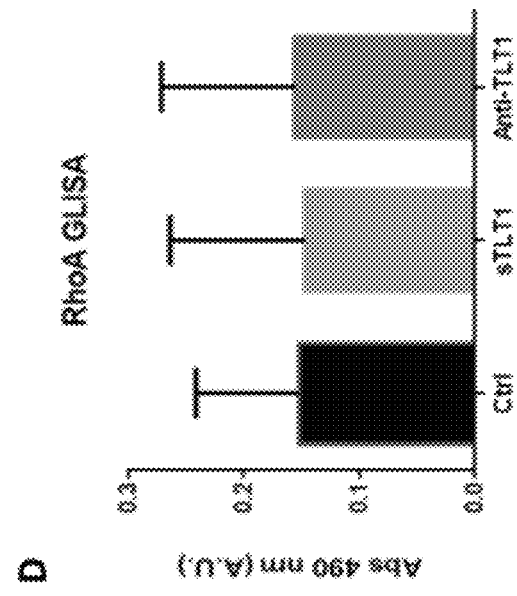

Effect of Soluble TLT-1 Effect in HUVECs Filopodia Formation and Cdc42 Activation As our previous results showed, a common observation upon addition of sTLT-1 to HUVECs is a strong binding of phalloidin to these cells. The polymerization of actin filaments in a regulated manner, at the leading tips of cells, allows for the generation of lamellopodia and filopodia in cells. Thus, we hypothesized that sTLT-1 actin polymerization in HUVECs could occur as a consequence of an event that requires this molecular process, such as filopodia formation. To examine the effect of sTLT-1 on endothelial cell filopodia formation, cultured HUVECs were added sTLT-1 (12.5 ng/µL) or no treatment and they were left incubating 24 hours at 37° C. Cells were fixed, stained with rhodamine phalloidin and compared to untreated control (FIG. 7A). Our results show that sTLT-1 induces the formation of filopodia on HUVECs compared to control cells without treatment.

Members of the Rho small GTPases, Rac1, RhoA, and Cdc42 are the leading regulators of filopodia and lamellopodia formation, crucial features of actively moving cells such as endothelial cells. To examine the activation of the small Rho GTPases upon the addition of sTLT-1, activation assays (G-LISA) were used. In these assays, cells were starved, added sTLT-1 (5.5 ng/µL) or no treatment, and incubated for 30 minutes at 37° C. After incubation, cells were washed with PBS 3 times, lysates were prepared following kit instructions, and same amounts of protein per treatment (0.5 mg/mL) were added to the G-LISA plate for each kit. Our results show that HUVECs exposed to sTLT-1 compared to non-treated control presented a significant activation of Cdc42 (Paired Student's T-test, p=0.010), and a non-significant activation of RhoA and Rac1 activation (FIG. 7 B-D). To test for Cdc42, Rac-1, and RhoA activation in these cells, small Rho GTPase activation assays (G-LISA) were performed. In these assays HUVECs were grown, added sTLT-1 or no treatment for 30 min, lysates were prepared and added to the G-LISA plates which had affinity towards activated Rac-1, RhoA and Cdc42. These experiments were performed a least three times and to test significance a Student's T-test (paired) was performed: Cdc42, *p=0.010, ****p=0.0001, Rac-1=n.s. and RhoA=n.s. Altogether, these results show that sTLT-1 is involved in the modulation of Rho small GTPases which control actin polymerization in endothelial cells and these cascades could be accountable for the promotion of filopodia formation in HUVECs.

Figure 8:
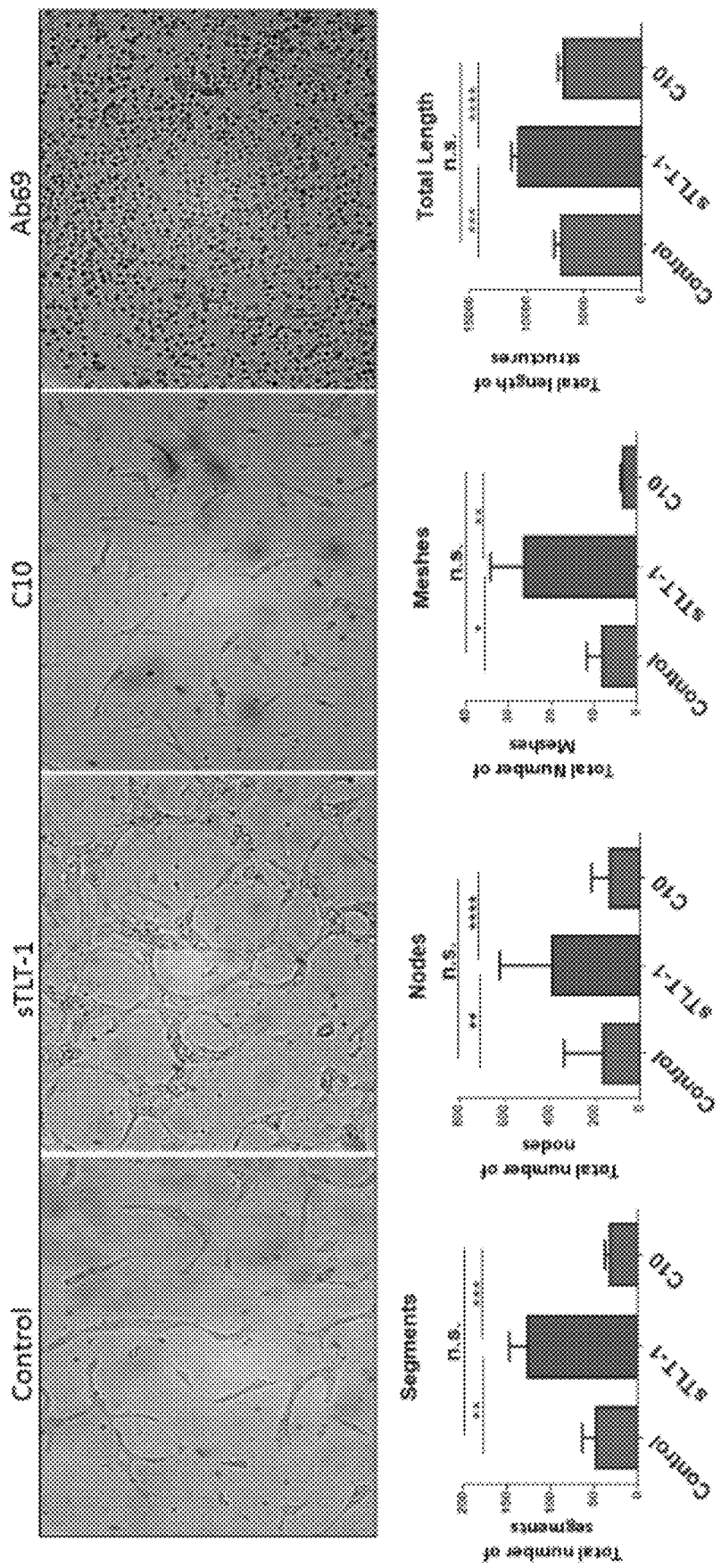
FIG. 8 shows that HUVECs treated with sTLT-1 show increased capillary tube formation which can be reversed by TLT-1 blocking antibody C10.

Tube Formation Assay in HUVECs Treated with sTLT-1 Shows Increased Capillary Formation As signaling cascades for cell migration and filopodia formation were activated by sTLT-1 in HUVECs, we hypothesized that sTLT1 would promote pro-angiogenic features such as increased capillary tube formation, which is also indicative of cell migration. In this assay, HUVECs were grown in Matrigel and these were untreated (Ctrl), added sTLT-1 (25 ng/µL), or added TLT-1 blocking antibody C10 (+C10) 120 ng/µL, or 100 µL of Antibody a69 hybridoma which showed no quantifiable structures. After 26 hrs of incubation at 37° C., cells were photographed and analyzed using Image J Angiogenesis Analyzer (n=3 experiments). Our results show that cells added sTLT-1 have significantly higher number of segments, nodes, meshes and total length of quantified structures, when compared to controls and C10 exposed HUVECs (FIG. 8). Student's T-test *p=0.05, p=<0.005, *p=<0.0005, ****p<0.00005. Interestingly, all of these are pro-angiogenic features that promote endothelial cell capillary tube formation, testing our hypothesis correct.

Cytokine Release after Exposure of HUVECs to sTLT-1

Figure 9:
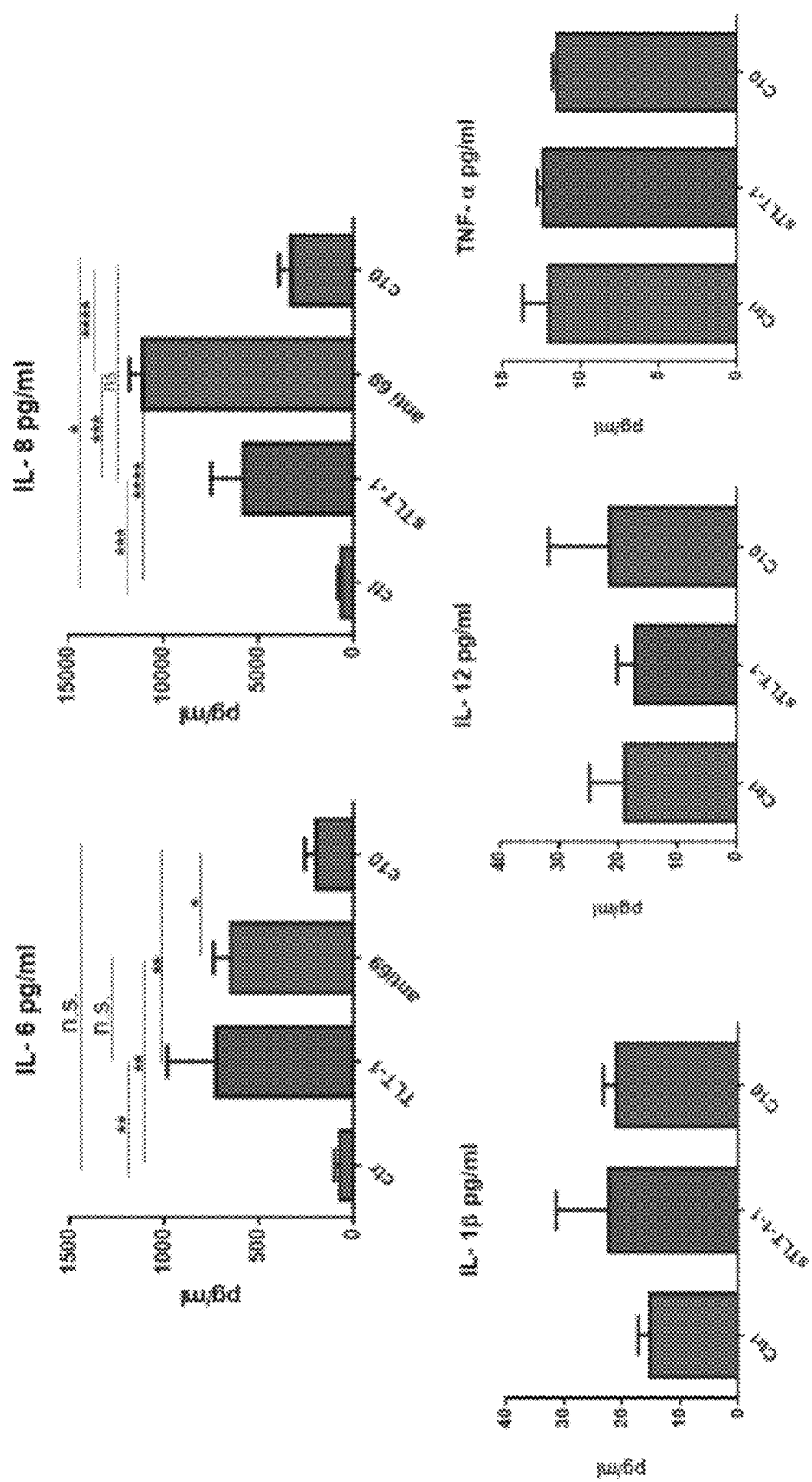
FIG. 9 shows that HUVECs release proangiogenic molecules interleukin 6 & 8 release after exposure to sTLT-1.

To test whether HUVECs pro-angiogenic features upon exposure of sTLT-1 were caused by the release of pro-angiogenic cytokines from HUVECs when exposed to sTLT-1, a human cytokine bead assay was used to detect eight different cytokines in supernatants of HUVECs exposed to sTLT-1. In this assay, sTLT-1 (25 ng/µL), C10 antibody+sTLT-1 (25 ng/µL) or no treatment, were added to HUVECs grown in the soluble basement membrane MATRIGEL® (Corning). The supernatant of these cells was obtained and assessed for cytokine release after 26 hrs. Cells incubated with sTLT-1 showed significant increases in the levels of interleukins 6 and 8 after when compared to controls (FIG. 9). The blocking, single-chain C10 antibody, kept a sustained effect decreasing the release of these cytokines almost to control levels. T-test *p=0.05, p=<0.005, *p=<0.0005, n.s.=not significant. The differences in IL-1β, IL-12, TNF-α and IL-10 production were not different between the three groups. These results show that sTLT-1 induces the release of pro-angiogenic cytokines IL-6 and IL-8 from HUVECs, which could explain why cells exposed to sTLT-1 have increased pro-angiogenic features such as segments, nodes, meshes, and promote migration in a tube formation assay.

Discussion

Several studies have shown that platelet's α-granules have subpopulations that are different based on their cargo molecules and released upon differential signaling. Deciphering the contents of these granules and how they are selectively released is crucial for our understanding on platelet function. A closer look on TLT-1 distribution in human platelets showed that it can be localized to a different type of granule that does not contain P-selectin. These findings support the idea that platelets granules, including α-granules, are heterogeneous in their cargo and show that TLT-1 and P-selectin are two of the molecules contributing to this heterogeneity. When we study the distribution of TLT-1 upon platelet spreading, compared to that of P-selectin, we observed that both proteins at 3 minutes of spreading in glass start off in the granulomere and disperse differently throughout time through the platelet's lamellopodia and filopodia. Interestingly, when platelets are activated with thrombin, most of the P-selectin and TLT-1 seem to be released from the granulomere and they colocalize especially in the marginal microtubules of the platelet. Thus, TLT-1 distribution throughout the platelet and colocalization with proteins like P-selectin, will depend on the platelet's activation pathway.

By performing double immunofluorescence studies, we were able to detect colocalization of TLT-1 with VEGF and endostatin containing—α-granules, but the colocalization with VEGF-containing α-granules was much greater compared to endostatin. The release of VEGF positive α-granules has been associated to pro-angiogenic, PAR-1 receptor signaling while PAR-4 has been associated to release of anti-angiogenic molecules. Our studies showed that TLT-1 responded to the same signaling pathway than VEGF, releasing sTLT-1 significantly more with the PAR-1 agonist TFFLR, than with the PAR-4 agonist AYPGK. The PAR receptors are both G-protein coupled receptors that induce downstream $G\alpha_{12/13}$ and $G\alpha_q$ signaling in platelets and lead to cytoskeletal rearrangements for platelet shape change and granule secretion, respectively. Studies with PAR-1 specific agonists have shown that SFFLR (in our case TFFLR which has higher selectivity for PAR-1 receptor over PAR-2) activates both $G\alpha_{12/13}$ and $G\alpha_q$ but has increased preference for the $G\alpha_q$. Taken together, these studies suggest that activation of platelets with a PAR-1 agonist, that preferentially activates $G\alpha_q$, promotes the secretion of granules that contain sTLT-1.

These studies showed for the first time that human recombinant sTLT-1 can be endocytosed by HUVECs, as colocalization of sTLT-1 Alexa 555 with early endosome antigen-1 (EEA-1) protein in HUVECs was found colocalizing with sTLT-1-Alexa 555 at 30 minutes. Colocalization with endosomal recycling markers (Rab 11) or degradation markers (Rab 7) was not observed at these time points. These results could imply a specific membrane component of either a receptor, a lipid or a glycosphingolipid/protein co-import in cells (endocytosis, translocation) through which sTLT-1 could perform its role on HUVECs.

After sTLT-1 was added to HUVECs, these cells showed significantly more actin polymerization, cell area increase, and filopodia formation, compared to controls without treatment. Synchronized actin polymerization on motile cells can lead to the formation of filopodia at the cell's edge. Filopodia have a crucial role in cell migration, since they allow chemotactic sensing (mainly through VEGF, bFGF, and angiopoietins), motility, and cell-cell interaction. So far, VEGF receptor 2, the neuropilins and PECAM-1 are the proteins identified to be directly involved in the promotion of filopodia formation on endothelial cells. Our studies propose that sTLT-1 adds to the list of proteins leading to the formation of filopodia on endothelial cells.

In the search of a pathway that could mediate the sTLT-1 effects observed on HUVECs, we were able to identify the first molecular cascade induced directly by the addition of sTLT-1 on endothelial cells: activation of small Rho GTPase Cdc42. This activation is known to promote cell motility by allowing the formation of filopodial structures on endothelial cells. The most recognized signaling cascade that activates Cdc42 in endothelial cells to promote actin polymerization and migration is the VEGF/VEGFR2 receptor pathway. Even though sTLT-1 has not been shown to promote the activation of VEGFR2, we have shown in our experiments that it activates some of the molecular cascades that lead to actin polymerization, such as the Cdc42 pathway, which are normally stimulated by pro-angiogenic molecules like VEGF. Accordingly, we propose a new mouse monoclonal antibody that recognizes the extracellular fragment of TLT-1, we named Antibody a69. This antibody, when added together with sTLT-1 in a G-LISA assay, was able to inhibit Cdc42 activation, demonstrating that the Cdc42 activation on HUVECs was specific to sTLT-1, and showing its potential as a novel sTLT-1 neutralizing antibody.

Growth of HUVECs in the basement membrane Matrigel, significantly stimulated the amounts of segments (tubes), nodes (tube connections), meshes (networks of thick lumens) and total length of these structures formed by HUVECs, inducing at least three proangiogenic features in these assays. On these experiments, C10 was able to block sTLT-1 proangiogenic effects, while Antibody a69 kept the cells in a stagnant mode after 26 hrs. These results show that sTLT-1 can promote the generation of proangiogenic features, leading to endothelial cell tube formation and migration. The blocking effects of Antibody C10 on this assay shows that this could move on forward to be tested in animals to determine if it blocks angiogenesis in vivo. The results with Antibody a69 suggest that this molecule could be causing apoptosis because the cells did not move significantly from their original place and did not form tubule-like structures in the basement membrane. Also, the high levels of cytokines released in these samples suggest that there was a cell death process. Overall these experiments suggest that upon addition of sTLT-1 on HUVECs grown on ECM, a possible mechanism that could explain in part the increased development of proangiogenic features could be through Cdc42 activation and downstream effectors of this protein, leading to actin polymerization and the generation of these structures. Complementing these results, we found that upon addition of sTLT-1 to HUVECS these cells released significantly more two well-known cytokines that promote proangiogenic features and cell migration: IL-6 and IL-8. These cytokines exert their effects mostly through VEGF and the activation of VEGFR2, and as we showed, the PAR-1 signaling that releases TLT-1 also releases VEGF. Therefore, release of IL-6 and IL8 in sTLT-1-activated HUVECs, could promote angiogenesis through the downstream release of VEGF and subsequent activation of VEGFR2 from endothelial cells. All this evidence led us to conclude that sTLT-1 has a new role promoting angiogenesis in HUVECs by promoting the release of cytokines involved in angiogenesis which induce the release of the most potent angiogenic molecule known, VEGF.

Figure 10:
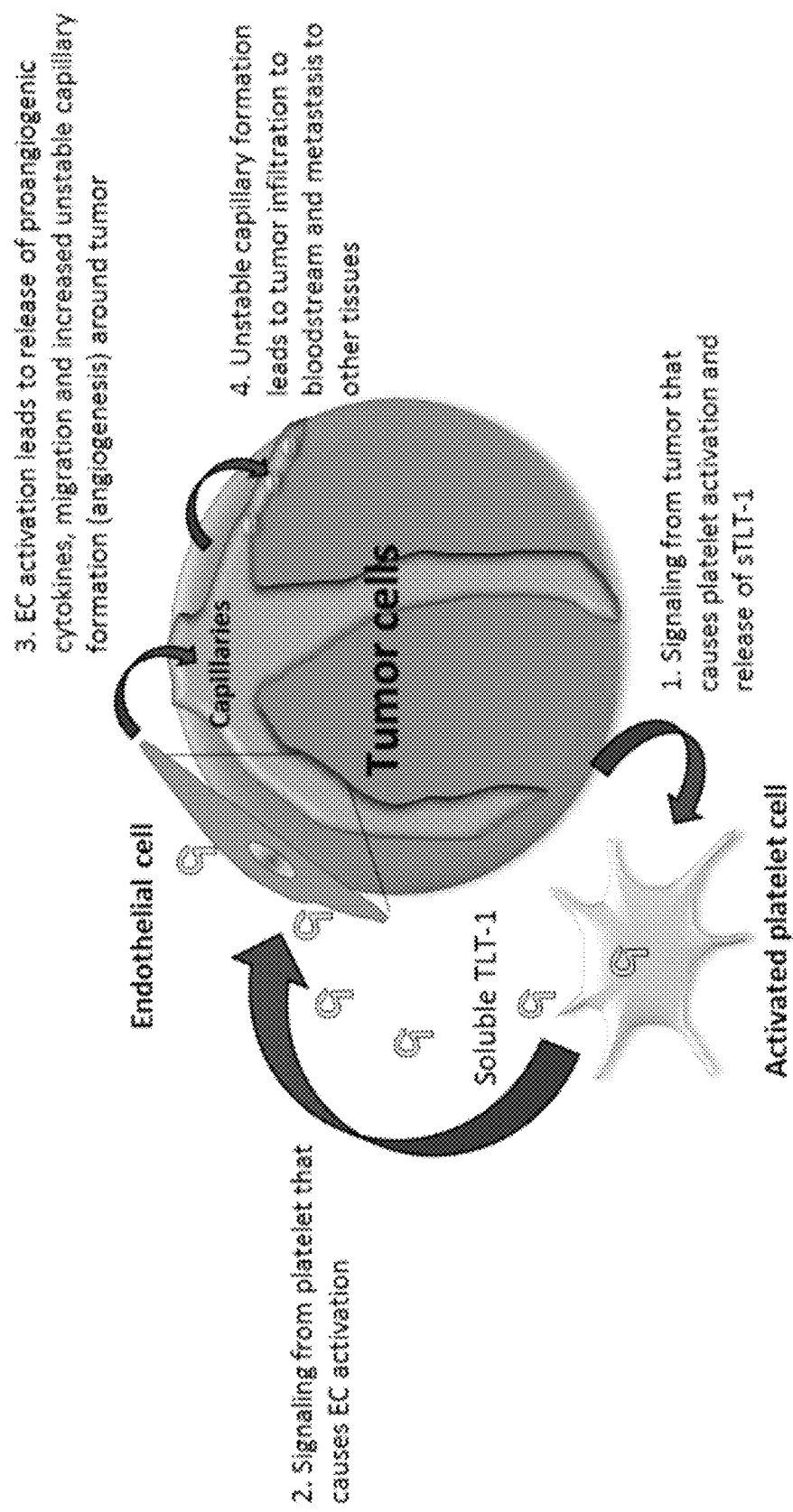
FIG. 10 illustrates the hypothetical model of sTLT-1 involvement in cancer and metastasis through a role in angiogenesis.

Both IL6 and IL8 have been shown to induce tumor growth, as blockade or silencing of these two cytokines significantly influence tumor growth in vivo and in vitro. Therefore, in a tumor microenvironment, where tumors are surrounded by platelet-activating compounds such as thrombin, sTLT-1 released from platelets can induce IL-6 and IL8 release from the endothelial cells surrounding the tumor, which would promote tumor growth. In a previous study, to make an assessment of disseminated intravascular coagulation in cancer-treated mice, levels of sTLT-1 were measured in the plasma from mice bearing MCF-7 xenografts (an aggressive, inflammatory breast cancer model) and subsequently treated with vehicle, titanocene or titanocenyl-pregnenolone (Ti-Preg) as the compounds to be tested. Levels of sTLT-1 in plasma of control mice with the tumor were significantly higher than mice with cancer exposed to anti-tumor treatment titanocenyl-pregnenolone. These results suggest that sTLT-1 levels in blood could correlate not only with DIC, but also with tumor progression. These studies have led us to hypothesize that TLT-1 plays a role in tumor development and cancer, possibly through a mechanism of angiogenesis regulation and ongoing studies are aiming towards testing this hypothesis (FIG. 10).

In conclusion, the present invention demonstrates the differential sTLT-1 distribution in human platelet's granules, colocalizing molecules in TLT-1's positive granules and uncover a specific release mechanism from platelets. They also demonstrate a direct molecular crosstalk between soluble TLT-1 and HUVECs, revealing a new role for sTLT-1 in angiogenesis. Through this invention we intend to expand the amount of therapeutic purposes that blocking or enhancing blood's sTLT-1 levels could bring in the near future.

The invention is a monoclonal antibody against human (ab69) and mouse (clones Triggering Receptor and (Clones Expressed in Myeloid TREM) cells—like transcript-1 or TLT-1. TLT-1 is an immune regulatory receptor found on platelets and megakaryocytes. Our studies in mice and humans have associated TLT-1 with cardiovascular disease, Cancer, obesity, angiogenesis, and inflammation. This antibody reverses the effects of TLT-1 on platelets and neutralize the effect of the soluble form of TLT-1 (sTLT-1) in our in vitro studies and therefore hold therapeutic potential. This antibody can also identify TLT-1 on platelets by flow cytometry, in western blots, by immunofluorescence, ELISA and immunoprecipitation giving it immediate use as a diagnostic tool for research and blood marker and/or treatment for diseases such as disseminated intravascular coagulation. Overcomes problems detecting the protein and facilitates research on TLT-1 function in humans. The Antibody can be used as intervention for any diseases that has or may have a TLT-1 component such as Disseminated Intravascular Coagulation (DIC), Cardiovascular disease (CVD) and cancers and should overcome the problem of blocking platelet function that leads to a bleeding diathesis.

Atherosclerosis remains the leading cause of death in both men a woman in the US despite remarkable advances in its understanding. It is well known that hyperlipidemia is a major risk factor for the progression and subsequent complications of atherosclerosis. However, the challenging and more elusive mechanisms involve the contribution of different atherogenic factors and cell populations, including platelets.

Once thought to be innocent bystanders in atherosclerosis progression, platelets have been shown to play an active role in disease progression. The identification of platelet-specific molecules like RANTES deposited at early stages of plaque formation as well as the characterization of platelets adhesion molecule P-selectin, has laid the foundation for the understanding that platelets play a crucial role in the initiation of atherosclerosis. Furthermore, platelets mediators can sustain an inflammatory state which promotes a vicious cycle of platelet activation and damage to the vessel wall.

We have previously characterized a platelet receptor which crucial roles in both inflammation and hemostasis. The Triggering Receptor Expressed on Myeloid Cells-(TREM)-like transcript-(TLT)-1, is sequestered in α-granules and brought to the surface upon activation. TLT-1 has both, membrane bound and soluble forms (sTLT-1) and the latter has been found to enhance platelet activation and platelet-endothelial cell interactions. Accordingly, TLT-1 null mice (trem11$^{-/-}$) are significantly more susceptible to lipopolysaccharide (LPS) septic challenge compared to their wild type counterparts and bleed in response to inflammatory challenge where control mice do not. These findings suggest that TLT-1 is an important link between inflammation and thrombosis and present a possible candidate receptor involved in conditions like cardiovascular disease. Key to these, is the fact that high sTLT-1 levels in plasma of sepsis patients have been found to correlate with several inflammatory diseases and moreover, correlate with disseminated intravascular coagulation better than the current clinical marker, D-dimers.

TLT-1 is a type 1 single pass receptor that is primarily found stored in the α-granules of platelets. There are three documented isoforms; full length (~37 kd), TLT-1sv (25 kd), and TLT-1s (22 kd). The first two of these variants have only been found on platelets and can be cleaved to release a biologically soluble fragment (sTLT-1). The third was identified on pre-osteoclasts in the bone marrow, but our group has cloned it out of the spleen, suggesting it is on other populations of splenic cells. We have identified the 22 kd form by flow cytometry on platelets and bone marrow derived macrophage precursors. The 25 kd form has been identified only in humans. TLT-1, sTLT-1, and TLT-1s are found in mice and humans. Our mouse model has removed the first two exons which removes the extracellular domain from platelets. TLT-1 is initiated from an alternative start site upstream of exon 3 and remains in the TLT-1 knockout mouse.

The antibody was produced against the TLT-1 extracellular domain (amino acids ~20-146) with the expressed intent of producing both a TLT-1 diagnostic agent and potential therapeutic agent against inflammatory diseases such as cardiovascular disease, diseases involving an increase in angiogenesis (such as Cancer), and inflammation. To date, we can demonstrate that our antibodies inhibit soluble TLT-1 induced-angiogenesis and neutrophil activation.

Our data shows that TLT-1 Antibody a69 can be used for flow cytometry, Enzyme-Linked Immuno Assays (ELISA), western blots, immunoprecipitation, and immunofluorescence. We also can show that it inhibits the angiogenic effects of sTLT-1 on endothelial cells and leading the cells to what appears to be apoptosis. Furthermore, we see an expressed inhibition of sTLT-1 induced/enhanced neutrophil activation in the presence of platelets. Based on these in vitro assays, we have a potential diagnostic for DIC (works for ELISA and thus can be used detect the presence of sTLT-1 during sepsis or cancer). Antibody a69 inhibits soluble TLT-1 induced angiogenesis in vitro suggesting a potential role in cancer therapy. In our mouse model, the murine antibodies demonstrate the therapeutic potential of the human antibodies. The murine antibodies which would be marketed for research purposes decrease vessel growth in tumors in addition to having the ability to western blot, immunoprecipitate, and work in flow cytometry and immunofluorescence assays. Other potential uses of our antibody include cardiovascular disease where our preliminary data show that the TLT-1 null mouse has smaller lesions that their apoE siblings and reagents against TLT-1 reduce platelet adherence to collagen surfaces, sepsis, and pulmonary diseases.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

We claim:

1. An anti-TLT-1 antibody, or antigen-binding fragment, comprising the following six hypervariable regions (HVRs):
   an HVR-H1 comprising the amino acid sequence of (SEQ ID NO: 1);
   an HVR-H2 comprising the amino acid sequence of (SEQ ID NO: 2);
   an HVR-H3 comprising the amino acid sequence of (SEQ ID NO: 3);
   an HVR-L1 comprising the amino acid sequence of (SEQ ID NO: 4);
   an HVR-L2 comprising the amino acid sequence of (SEQ ID NO: 5); and
   an HVR-L3 comprising the amino acid sequence of (SEQ ID NO: 6).

2. The antibody or antigen-binding fragment of claim 1, wherein the antibody further comprises the following heavy chain variable region FRs:
   an FR-H1 comprising the amino acid sequence of (SEQ ID NO: 7);
   an FR-H2 comprising the amino acid sequence of (SEQ ID NO: 8); and
   an FR-H3 comprising the amino acid sequence of (SEQ ID NO: 9).

3. The antibody or antigen-binding fragment of claim 1, wherein the antibody further comprises the following light chain variable region framework regions (FRs):
   an FR-L1 comprising the amino acid sequence of (SEQ ID NO: 10);
   an FR-L2 comprising the amino acid sequence of (SEQ ID NO: 11); and
   an FR-L3 comprising the amino acid sequence of (SEQ ID NO: 12).

4. The antibody or antigen-binding fragment of claim 1, wherein the antibody is a monoclonal antibody.

5. The antibody or antigen-binding fragment of claim 1, wherein the antibody is a mouse antibody against human TLT-1.

6. The antibody or antigen-binding fragment of claim 1, wherein the antibody is a IgG class antibody.

7. The antibody or antigen-binding fragment of claim 1, wherein the antibody is a IgG2b antibody.

8. The antibody or antigen-binding fragment of claim 1, wherein the antibody is an antibody fragment that binds to a CDR3 loop of TLT-1.

9. A method for detecting the presence of TLT-1 protein on platelets, the method comprising:
- exposing a platelet-containing sample to an antibody, or antigen-binding fragment, comprising the following six hypervariable regions (HVRs):
- an HVR-H1 comprising the amino acid sequence of (SEQ ID NO: 1);
- an HVR-H2 comprising the amino acid sequence of (SEQ ID NO: 2);
- an HVR-H3 comprising the amino acid sequence of (SEQ ID NO: 3);
- an HVR-L1 comprising the amino acid sequence of (SEQ ID NO: 4);
- an HVR-L2 comprising the amino acid sequence of (SEQ ID NO: 5);
- an HVR-L3 comprising the amino acid sequence of (SEQ ID NO: 6); and
- detecting the presence of said TLT-1 protein on the platelets by determining binding of said antibody, or antigen-binding fragment, to the TLT-1 protein on said platelets.

10. The method of claim 9, wherein said binding is determined by at least one of: flow cytometry, western blots, immunofluorescence, immunoprecipitation, and ELISA.

11. The method of claim 9, wherein antibody is an antibody fragment that binds to a CDR3 loop of TLT-1.

\* \* \* \* \*

SEQUENCE LISTING

<160> NUMBER OF SEQ ID NOS: 12

<210> SEQ ID NO 1
<211> LENGTH: 15
<212> TYPE: DNA
<213> ORGANISM: Artificial Sequence
<220> FEATURE:
<223> OTHER INFORMATION: Heavy Chain Variable Region - CDR1

<400> SEQUENCE: 1
acccactgga tgcag      15

<210> SEQ ID NO 2
<211> LENGTH: 51
<212> TYPE: DNA
<213> ORGANISM: Artificial Sequence
<220> FEATURE:
<223> OTHER INFORMATION: Heavy Chain Variable Region - CDR2

<400> SEQUENCE: 2
gctatttatc ctggagatgg taatactaga tacactcaga atttcaaggg c      51

<210> SEQ ID NO 3
<211> LENGTH: 33

```
<212> TYPE: DNA
<213> ORGANISM: Artificial Sequence
<220> FEATURE:
<223> OTHER INFORMATION: Heavy Chain Variable Region - CDR3

<400> SEQUENCE: 3
tggggcgcag ggaccacggt caccgtctcc tca                              33

<210> SEQ ID NO 4
<211> LENGTH: 33
<212> TYPE: DNA
<213> ORGANISM: Artificial Sequence
<220> FEATURE:
<223> OTHER INFORMATION: Light Chain Variable Region - CDR1

<400> SEQUENCE: 4
agggccagcc aaagtcttag caacaaccta cac                              33

<210> SEQ ID NO 5
<211> LENGTH: 18
<212> TYPE: DNA
<213> ORGANISM: Artificial Sequence
<220> FEATURE:
<223> OTHER INFORMATION: Light Chain Variable Region - CDR2

<400> SEQUENCE: 5
gcttcccagt ccatctct                                               18

<210> SEQ ID NO 6
<211> LENGTH: 31
<212> TYPE: DNA
<213> ORGANISM: Artificial Sequence
<220> FEATURE:
<223> OTHER INFORMATION: Light Chain Variable Region - CDR3

<400> SEQUENCE: 6
caacagagta acagctggcc gtacacgttc g                                31

<210> SEQ ID NO 7
<211> LENGTH: 90
<212> TYPE: DNA
<213> ORGANISM: Artificial Sequence
<220> FEATURE:
<223> OTHER INFORMATION: Heavy Chain Variable Region Framework Region -
      FWR1

<400> SEQUENCE: 7
caggttcagc tgcagcagtc tggggctgag ctggcaagac ctggggcttc agtgaagttg   60
tcctgcaagg cttctggcta cacctttact                                   90

<210> SEQ ID NO 8
<211> LENGTH: 42
<212> TYPE: DNA
<213> ORGANISM: Artificial Sequence
<220> FEATURE:
<223> OTHER INFORMATION: Heavy Chain Variable Region Framework Region -
      FWR2

<400> SEQUENCE: 8
tgggtaaaac agaggcctgg acagggtctg gaatggattg gg                     42

<210> SEQ ID NO 9
<211> LENGTH: 96
<212> TYPE: DNA
<213> ORGANISM: Artificial Sequence
<220> FEATURE:
```

```
<223> OTHER INFORMATION: Heavy Chain Variable Region Framework Region -
      FWR3

<400> SEQUENCE: 9
aaggccacat tgactgcaga tatatcctcc agcaccgcct acatgcaact cagcagcttg    60
gcatctgagg actctgcggt ctattactgt gcaaga                              96

<210> SEQ ID NO 10
<211> LENGTH: 69
<212> TYPE: DNA
<213> ORGANISM: Artificial Sequence
<220> FEATURE:
<223> OTHER INFORMATION: Light Chain Variable Region Framework Region -
      FWR1

<400> SEQUENCE: 10
gatattgtgc taactcagtc tccagccacc ctgtctgtga ctccaggaga tagcgtcagt    60
ctttcctgc                                                            69

<210> SEQ ID NO 11
<211> LENGTH: 48
<212> TYPE: DNA
<213> ORGANISM: Artificial Sequence
<220> FEATURE:
<223> OTHER INFORMATION: Light Chain Variable Region Framework Region -
      FWR2

<400> SEQUENCE: 11
tggtatcaac aaaaatcaca tgagtctcct aggcttctca tcaattat                 48

<210> SEQ ID NO 12
<211> LENGTH: 96
<212> TYPE: DNA
<213> ORGANISM: Artificial Sequence
<220> FEATURE:
<223> OTHER INFORMATION: Light Chain Variable Region Framework Region -
      FWR3

<400> SEQUENCE: 12
gggatcccct ccaggttcag tggcagtgga tcagggacag atttcactct ccgtatcaac    60
agtgtggaga ctgaagattt tggaatgtat ttctgt                              96
```